US00RE37952E

(19) United States
(12) Reissued Patent
Schweighoffer et al.

(10) Patent Number: US RE37,952 E
(45) Date of Reissued Patent: Dec. 31, 2002

(54) GRB3-3 CDNA AND POLYPEPTIDES

(75) Inventors: Fabien Schweighoffer, Vincennes (FR); Bruno Tocque, Courbevoie (FR)

(73) Assignee: Aventis Pharma S.A., Antony Cedex (FR)

(21) Appl. No.: 09/641,640

(22) PCT Filed: May 9, 1994

(86) PCT No.: PCT/FR94/00542

§ 371 (c)(1), (2), (4) Date: Mar. 13, 1996

(87) PCT Pub. No.: WO95/07981

PCT Pub. Date: Mar. 23, 1995

Related U.S. Patent Documents

Reissue of:
(64) Patent No.: 5,831,048
Issued: Nov. 3, 1998
Appl. No.: 08/612,857
Filed: Mar. 13, 1996

(30) Foreign Application Priority Data

Sep. 15, 1993 (FR) ..... 93 10971

(51) Int. Cl.[7] ..... C07H 21/04; C12N 15/63
(52) U.S. Cl. ..... 536/23.1; 435/320.1; 435/6; 435/455; 435/471; 536/24.3; 536/24.5; 530/350
(58) Field of Search ..... 435/6, 320.1, 455, 435/471; 536/23.1, 24.3, 24.5; 530/350

(56) References Cited

U.S. PATENT DOCUMENTS 5,434,064 A 7/1995 Schlessinger et al. ..... 435/71.2

FOREIGN PATENT DOCUMENTS

WO WO 9407913 4/1994

OTHER PUBLICATIONS

Lowenstein et al., "The SH2 and SH3 Domain–containing Protein GRB2 Links Receptor Tyrosine Kinases to Ras Signaling," Cell., vol. 70, pp. 431–442 (1992).

Matuoka et al., "Cloning of ASH, a Ubiquitous Protein Composed of One Src Homology Region (SH) 2 and Two SH3 Domains, From Human and Rat cDNA Libraries," Proc. Nat'l. Acad. Sci., USA, vol. 89, pp. 9015–9019 (1992).

Rey et al., "A Role for Grb2 in Apoptosis?" Cell Death and Diff., vol. 2, pp. 105–111 (1995).

Suen et al., "Molecular Cloning of the Mouse Grb2 Gene: Differential Interaction of the Grb2 Adaptor Protein with Epidermal Growth Factor and Nerve Growth Factor Receptors," Mol. Cell. Biol., vol. 13, pp. 5500–5512 (1993).

Watanabe et al., "Splicing Isoforms of Rat Ash/Grb2. Isolation and Characterization of the cDNA and genomic DNA Clones and Implications for the Physiological Roles of the Isoforms," J. Biol. Chem., vol. 270, pp. 13733–13739 (1995).

*Primary Examiner*—Lisa B. Arthur
*Assistant Examiner*—Jeanine Goldberg
(74) *Attorney, Agent, or Firm*—Finnegan, Henderson, Farabow, Garrett & Dunner, L.L.P.

(57) ABSTRACT

The present invention relates to the Grb3-3 protein, nucleotide sequence encoding this protein, and variants thereof, such as antisense sequences. The invention further relates to vectors comprising these sequences and to methods for inducing cell death.

30 Claims, 5 Drawing Sheets

NIH3T3

+Grb3-3

Marker

NIH3T3

+Grb3-3

+Grb2

+Grb3-3 G162R

+Grb2 G203R

+Grb3-3 +Grb2

+Grb3-3 +Grb2G203R

GRB3-3 CDNA AND POLYPEPTIDES

Figure 1:
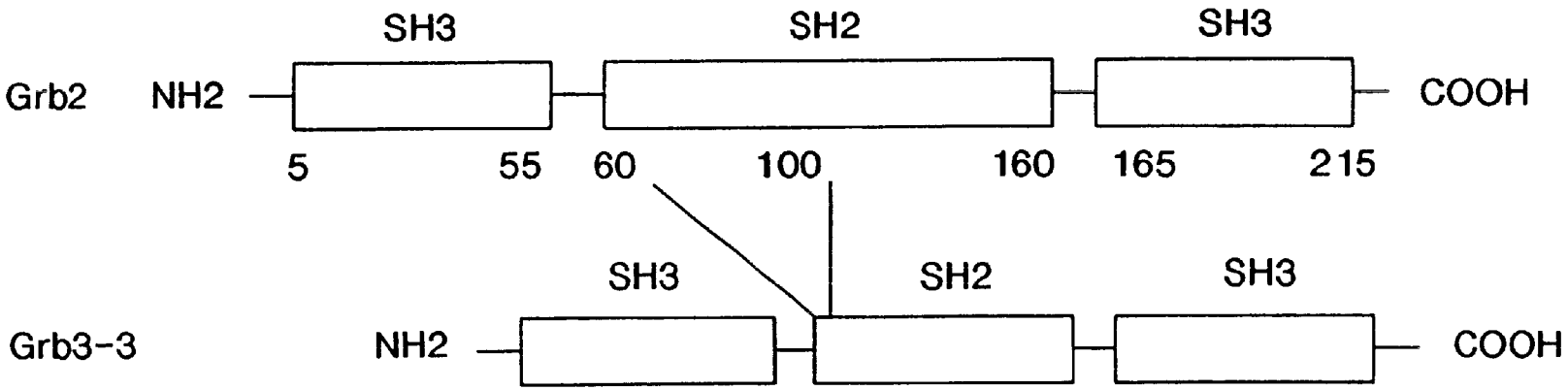

Matter enclosed in heavy brackets [ ] appears in the original patent but forms no part of this reissue specification; matter printed in italics indicates the additions made by reissue.

*This application is a reissue application of U.S. application Ser. No. 08/612,857, filed Mar. 13, 1996, which is a §371 national stage filing of PCT/FR94/00542, filed May 9, 1994.*

The present invention relates to a new gene, designated Grb3-3, its variants, and their uses, especially in anti-cancer gene therapy.

Various genes, called oncogenes and suppressor genes, are involved in the control of cell division. Among them, the ras genes and their products generally designated p21 proteins, play a key role in the control of cell proliferation in all eukaryotic organisms where they have been searched out. In particular, it has been shown that certain specific modifications of these proteins cause them to lose their normal control and lead them to become oncogenic. Thus, a large number of human tumours have been associated with the presence of modified ras genes. Likewise, an overexpression of these p21 proteins can lead to a deregulation of cell proliferation. An understanding of the exact role of these p21 proteins in cells, of their mode of operation and their characteristics therefore constitutes a major stake for the understanding and the therapeutic approach to carcinogenesis.

Various factors involved in the ras-dependent signalling pathway have been identified. Among these are the Grb2 gene which encodes a protein of 23–25 kDa having a SH3-SH2-SH3 structure (Lowenstein et al., Cell 70 (1992) 431; Matuoka et al., PNAS 89 (1992) 9015). The product of the Grb2 gene appears to interact with the tyrosine phosphorylated proteins via its SH2 domain, and with a factor for exchange of GDP of the SOS class via its SH3 domain (Egan et al., Nature 363 (1993) 45). It would thus be one of the components of the transformant activity of the product of the ras gene. The present invention derives from the demonstration of the cloning and characterization of an isoform of the Grb2 gene, designated Grb3-3, possessing a deletion in the SH2 domain. This gene is expressed in adult tissues: the corresponding mRNA is present in the form of a single band of 1.5 kb, and is translated into a 19 kDa protein. Because of its deletion in the SH2 domain, the product of the Grb3-3 gene is no longer capable of interacting with the tyrosine phosphorylated proteins (phosphorylated EGF receptor), but it retains the capacity to interact with the proline-rich domains of the SOS proteins. Because of its deletion, the product of the Grb3-3 gene is thus capable of preventing the cellular effects of the product of the Grb2 gene. The transfer of this gene in vivo, or of variants thereof, including antisense sequences, therefore makes it possible to interfere with the processes of proliferation, differentiation and/or cell death.

A first subject of the invention therefore relates to a nucleotide sequence comprising all or part of the Grb3-3 gene (sequence SEQ ID No. 1).

Another subject of the invention relates to a nucleotide sequence derived from the sequence SEQ ID No. 1 and capable of inhibiting, at least partially, the expression of the Grb2 or Grb3-3 protein. In particular, the invention relates to the antisense sequences whose expression in a target cell makes it possible to control the transcription of cellular mRNAs. Such sequences can for example be transcribed, in the target cell, into RNAs complementary to the cellular mRNAs Grb2 or Grb3-3 and thus block their translation into protein, according to the technique described in patent EP 140 308. Such sequences may consist of all or part of the nucleic sequence SEQ ID No. 1, transcribed in the reverse orientation.

As indicated above, Grb2 is a protein which is at least bifunctional, and which is anchored via its SH2 domain to specific sequences phosphorylated at the tyrosine, and via its two SH3 domains, to the exchange factors of the SOS family. Grb3-3 having lost its capacity to associate with proteins phosphorylated at the tyrosine can therefore only form a complex with the SOS proteins. Grb3-3 can therefore prevent the recruitment of the Grb2-SOS complex by the receptors of the self-phosphorylated growth factors or by associated proteins which are also phosphorylated at the tyrosine such as HSC or IRS1. Grb3-3 being capable of blocking this recruitment, it is capable of blocking mytogenic pathways and of inducing cell death. The Applicant has indeed demonstrated that the Grb3-3 protein was expressed during certain physiological processes such as for example the maturation of the thymus in rats. The Applicant has also shown that Grb3-3 is capable of inducing cell death by apoptosis of various cell types. It was possible to detect these completely advantageous properties (i) by injecting recombinant protein into the 3T3 fibroblasts and (ii) by transferring the sequence encoding Grb3-3 into the 3T3 cells (Example 4). Grb3-3 is therefore capable of inducing the cellular death of viable cells such as immortalized, cancer or embryonic cells. As shown in the examples, Grb2 is capable of preventing the effects of Grb3-3.

Moreover, a search for the expression of Grb3-3 carried out during the infection of lymphocytic cells by the HIV virus made it possible to show that the massive viral production observed 7 days after the infection is correlated with an overexpression of the Grb3-3 mRNA by the infected cells (Example 5). This experiment shows that eliminating or blocking the cellular effects of Grb3-3 can also make it possible to maintain alive cells infected especially with HIV, and thus allow the T4 lymphocytes to continue to play a role of immune defence. In this respect, the invention also relates to the use of compounds capable of eliminating or blocking, at least partially, the cellular effects of Grb3-3 for the preparation of a pharmaceutical composition intended for the treatment of AIDS. More particularly, the compounds used may be:

genetic antisense sequences such as those defined above, oligonucleotides specific to Grb3-3, modified or otherwise for better stability or bioavailability (phosphorothioates, intercalating agents and the like). They may be preferably oligonucleotides covering the coding sequence localized between the N-terminal SH3 domain and the residual SH2 domain, any sequence whose transfer into the infected cells induces an overexpression of Grb2.

The nucleic acid sequences according to the invention can be used as such, for example after injection into man or animals, to induce a protection or to treat cancers. In particular, they can be injected in the form of naked DNA according to the technique described in application WO 90/11092. They can also be administered in complexed form, for example with DEAE-dextran (Pagano et al., J. Virol. 1 (1967) 891), with nuclear proteins (Kaneda et al., Science 243 (1989) 375), with lipids (Felgner et al., PNAS 84 (1987) 7413), in the form of liposomes (Fraley et al., J. Biol. Chem. 255 (1980) 10431), and the like.

Preferably, the nucleic acid sequences according to the invention form part of a vector. The use of such a vector indeed makes it possible to improve the administration of the nucleic acid into the cells to be treated, and also to increase its stability in the said cells, which makes it possible to obtain a durable therapeutic effect. Furthermore, it is possible to introduce several nucleic acid sequences into the same vector, which also increases the efficacy of the treatment.

The vector used may be of diverse origin, as long as it is capable of transforming animal cells, preferably human tumour cells. In a preferred embodiment of the invention, a viral vector is used which can be chosen from adenoviruses, retroviruses, adeno-associated viruses (AAV), herpes virus, cytomegalovirus (CMV), vaccinia virus and the like. Vectors derived from adenoviruses, retroviruses or AAVs incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

The present invention therefore also relates to any recombinant virus comprising, inserted into its genome, a nucleic acid sequence as defined before.

Advantageously, the recombinant virus according to the invention is a defective virus. The term "defective virus" designates a virus incapable of replicating in the target cell. Generally, the genome of the defective viruses used within the framework of the present invention is therefore devoid of at least the sequences necessary for the replication of the said virus in the infected cell. These regions can either be removed (completely or partially), or rendered non-functional, or substituted by other sequences and especially by the nucleic acid of the invention. Preferably, the defective virus nevertheless conserves the sequences of its genome which are necessary for the encapsulation of the viral particles.

It is particularly advantageous to use the nucleic acid sequences of the invention in a form incorporated in an adenovirus, an AAV or a defective recombinant retrovirus.

As regards adenoviruses, various serotypes exist whose structure and properties vary somewhat, but which are not pathogenic for man, and especially non-immunosuppressed individuals. Moreover, these viruses do not integrate into the genome of the cells which they infect, and can incorporate large fragments of exogenous DNA. Among the various serotypes, the use of the type 2 or 5 adenoviruses (Ad2 or Ad5) is preferred within the framework of the present invention. In the case of the Ad5 adenoviruses, the sequences necessary for the replication are the E1A and E1B regions.

The defective recombinant viruses of the invention can be prepared by homologous recombination between a defective virus and a plasmid carrying, inter alia, the nucleotide sequence as defined above (Levrero et al., Gene 101 (1991) 195; Graham, EMBO J. 3(12)(1984) 2917). The homologous recombination is produced after co-transfection of the said viruses and plasmid into an appropriate cell line. The cell line used should preferably (i) be transformable by the said elements, and (ii), contain sequences capable of complementing the part of the genome of the defective virus, preferably in integrated form so as to avoid the risks of recombination. As example of a line which can be used for the preparation of defective recombinant adenoviruses, there may be mentioned the human embryonic kidney line 293 (Graham et al., J. Gen. Virol. 36 (1977) 59) which contains especially, integrated into its genome, the left part of the genome of an Ad5 adenovirus (12%). As example of a line which can be used for the preparation of defective recombinant retroviruses, there may be mentioned the CRIP line (Danos and Mulligan, PNAS 85 (1988) 6460).

Then the viruses which have multiplied are recovered and purified according to conventional molecular biology techniques.

The subject of the present invention is also a pharmaceutical composition containing at last one recombinant virus or a nucleotide sequence as defined above.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected, optionally directly into the tumour to be treated. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses of nucleic acids (sequence or vector) used for the administration can be adapted as a function of various parameters, and in particular as a function of the mode of administration used, of the relevant pathology, of the nucleic acid to be expressed, or alternatively of the desired duration of treatment. Generally, with regard to the recombinant viruses according to the invention, the latter are formulated and administered in the form of doses of between $10^4$ and $10^{14}$ pfu/ml, and preferably $10^6$ to $10^{10}$ pfu/ml. The term pfu ("plaque forming unit") corresponds to the infectivity of a virus solution, and is determined by infecting an appropriate cell culture and measuring, generally after 48 hours, the number of plaques of infected cells. The techniques for determining the pfu titer of a viral solution are well documented in the literature.

Such pharmaceutical compositions can be used in man, for the treatment and/or prevention of cancer. In particular the products of the invention are capable of modulating the activity of ras proteins, they make it possible to intervene in the cancer development process, and in particular, they can inhibit the activity of oncogenes whose transformant activity depends on a p21-functional GAP interaction. Numerous cancers have indeed been associated with the presence of oncogenic ras proteins. Among the cancers most often containing mutated ras genes, there may be mentioned especially adenocarcinomas of the pancreas, of which 90% have a Ki-ras oncogene mutated on the twelfth codon (Almoguera et coll., Cell 53 (1988) 549), adenocarcinomas of the colon and cancers of the thyroid (50%), or carcinomas of the lung and myeloid leukaemias (30%, Bos, J. L. Cancer Res. 49 (1989) 4682). More generally, the compositions according to the invention can be used for treating any type of pathology in which an abnormal cell proliferation is observed, by inducing apoptosis, as well as any pathology characterized by a cell death by apoptosis (AIDS, Huntington's chorea, Parkinson), by means of compounds which block the effects of Grb3-3 (antisense in particular).

The present invention will be more fully described with the aid of the following examples which should be considered as illustrative and non-limiting.

LEGEND TO THE FIGURES

FIG. 1: schematic representation of the structural domains of Grb2 and Grb3-3.

Figure 2:
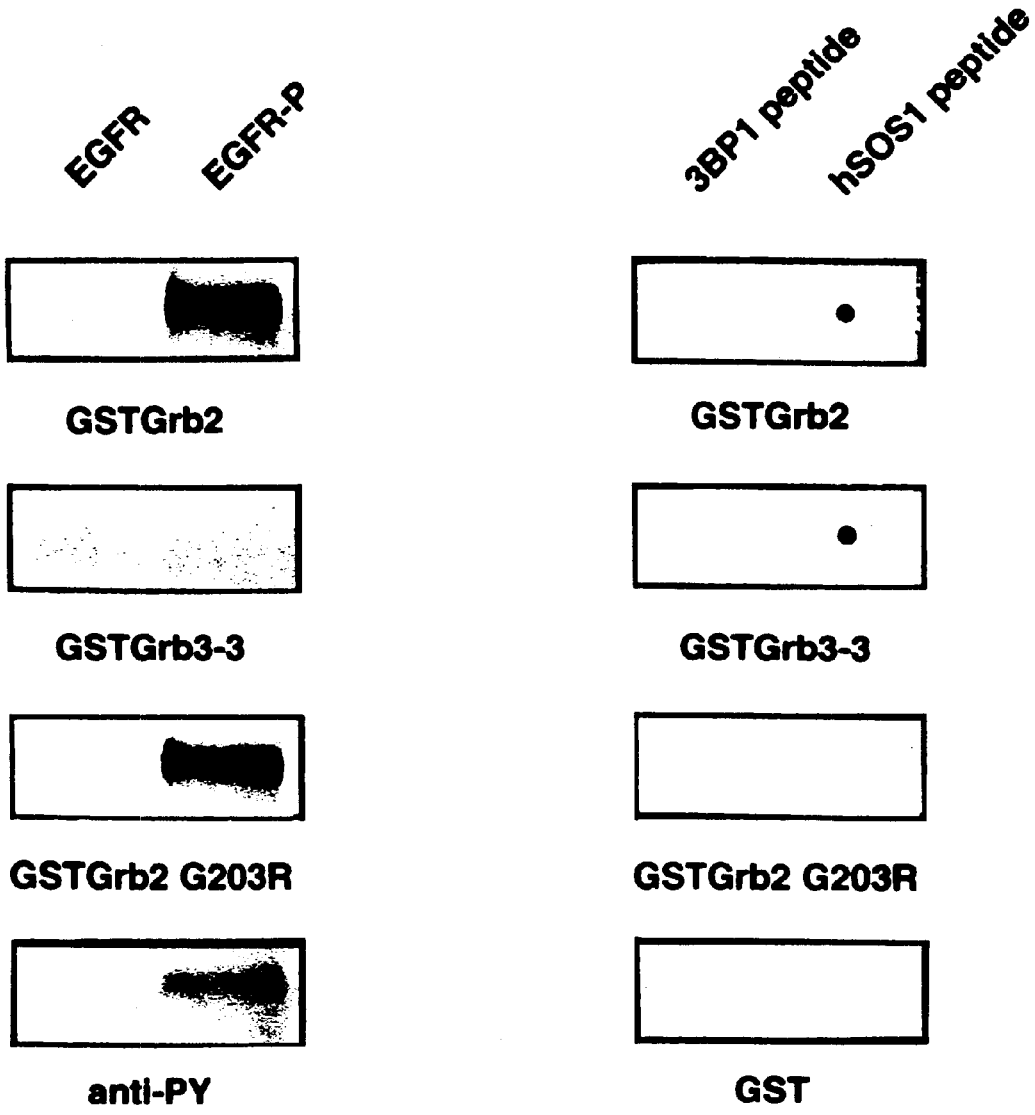

FIG. 2: study of the binding of Grb3-3 to the EGF receptor (FIG. 2a) and to proline-rich peptides (FIG. 2b).

Figure 3:
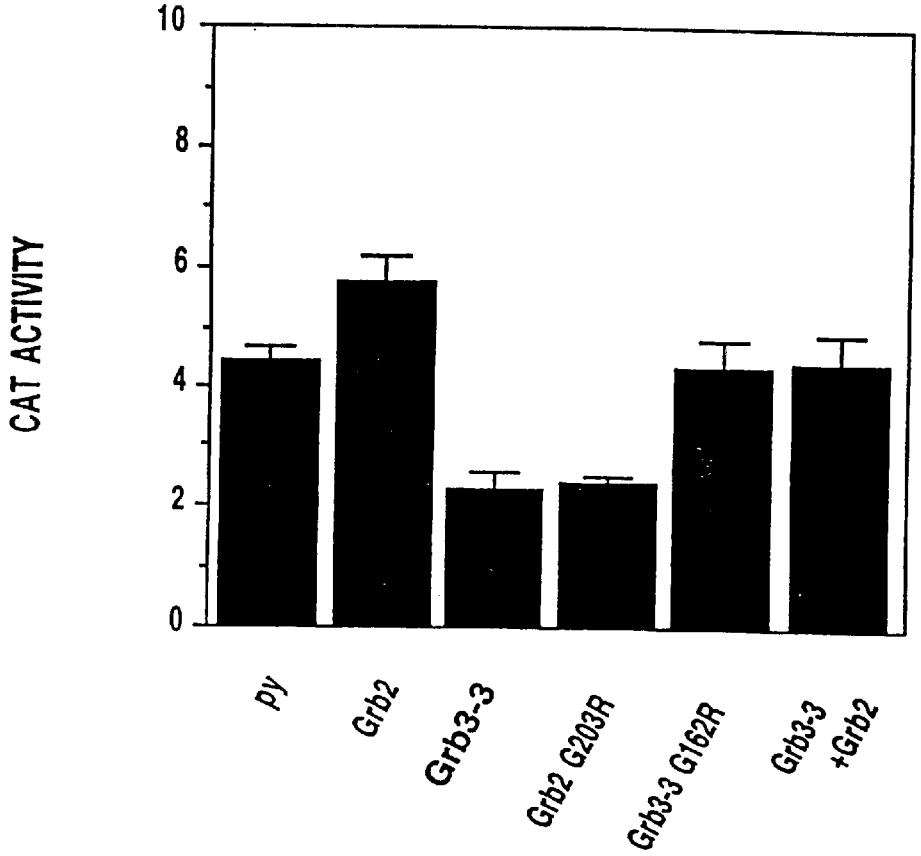

FIG. 3: effect of Grb3-3 on the transactivation, by ras, of an RRE derived from the polyoma virus enhancer.

Figure 4A:
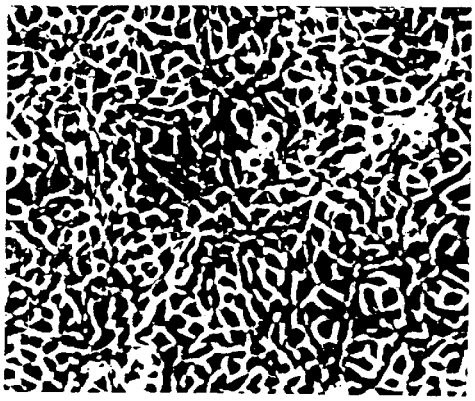
Figure 4B:
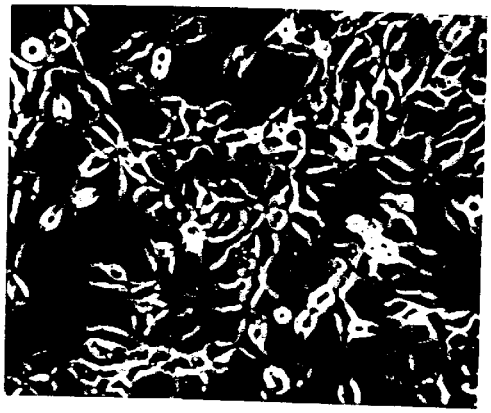
Figure 4C:
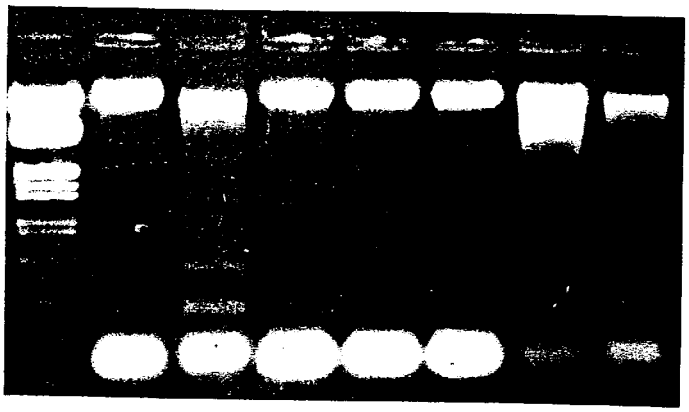

FIG. 4: demonstration of Grb3-3-induced cell death on 3T3 fibroblasts.

Figure 5:
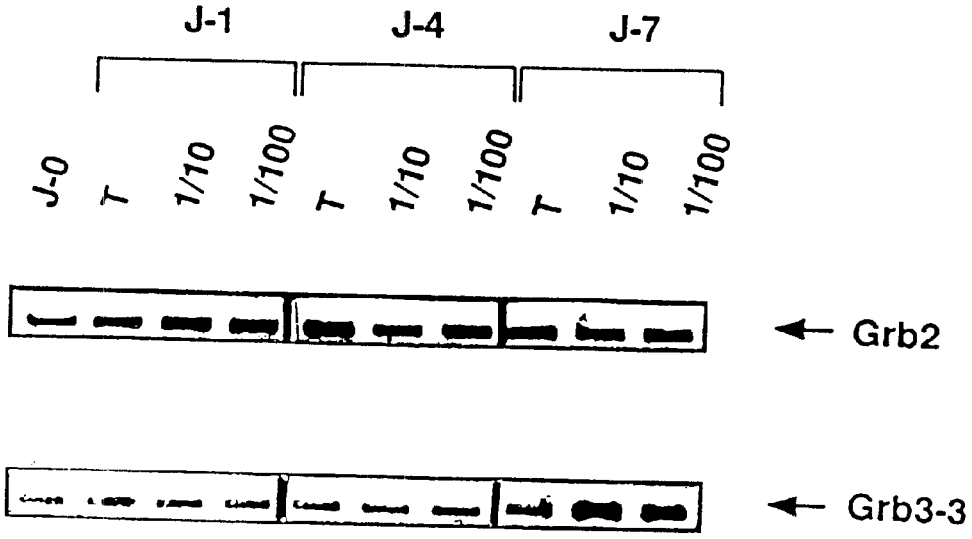

FIG. 5: demonstration of the expression of Grb3-3 in cells infected with the HIV virus.

GENERAL MOLECULAR BIOLOGY TECHNIQUES

The methods conventionally used in molecular biology, such as preparative extractions of plasmid DNA, centrifugation of plasmid DNA in caesium chloride gradient, electrophoresis on agarose or acrylamide gels, purification of DNA fragments by electroelution, extraction of proteins with phenol or phenolchloroform, DNA precipitation in saline medium with ethanol or isopropanol, transformation in Escherichia coli, and the like are well known to persons skilled in the art and are abundantly described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322 and pUC type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be carried out by the Klenow fragment of DNA polymerase I of E. coli (Biolabs) according to the specifications of the supplier. The destruction of the protruding 3' ends is carried out in the presence of phage T4 DNA polymerase (Biolabs) used according to the recommendations of the manufacturer. The destruction of the protruding 5' ends is carried out by a controlled treatment with S1 nuclease.

The site-directed mutagenesis in vitro with synthetic oligodeoxynucleotides can be carried out according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et a.l, Science 230 (1985) 1350–1354; Mullis K. B. et Faloona F. A., Meth. Enzym. 155 (1987) 335–350] can be carried out using a "DNA thermal cycler" (Perkin Elmer Cetus) according to the specifications of the manufacturer.

The verification of the nucleotide sequences can be carried out by the method developed by Sanger et al. [Proc. Natl. Acad. Sci. USA, 74 (1977) 5463–5467] using the kit distributed by Amersham.

EXAMPLES

1. Isolation of the Grb3-3 gene

The Grb3-3 gene was isolated by screening a human DNA library by means of a probe derived from the sequence of the Grb2 gene.

500,000 lambda gt11 recombinant phages carrying DNA fragments derived from a human placenta library (Clontech) were screened by means of a probe derived from the sequence of the Grb2 gene. The probe used corresponds to the first 8 amino acids of the Grb2 protein, and has the following sequence:

ATGGAAGCCATCGCCAAATATGAC (SEQ ID No. 3)

10 positive clones were thus identified. The insert of these 10 clones was isolated in the form of EcoRI fragments, cloned into the plasmid M13mp18 and sequenced. Among these 10 clones, 9 carried inserts identical to the Grb2 sequence. Only one of them carried an insert of a size smaller than the Grb2 gene, because of a deletion in the SH2 domain (FIG. 1). Analysis of the remaining sequence revealed a perfect identity with the corresponding regions of Grb2, including in the non-coding 5' and 3' regions. The open reading frame of this clone encodes a protein of 177 amino acids (SEQ ID No. 2), containing 2 SH3 domains bordering an incomplete SH2 domain (FIG. 1). The amino acids deleted in the SH2 domain (residues 60 to 100 of the Grb2 protein) correspond to the residues involved in the binding of Grb2 to the peptides containing phosphorylated tyrosines.

2. Binding activity of the Grb3-3 protein

As indicated above, the Grb2 protein is the mediator of the interaction between the phosphorylated growth factor receptors and the SOS factors. This example demonstrates that the Grb3-3 protein is incapable of interacting with the phosphorylated EGF receptor but that it conserves its capacity to interact with a proline-rich peptide derived from the sequence of the human SOS1 factor.

The binding capacity of Grb3-3 was studied using biotinylated Glutathione-S-transferase (GST) fusion proteins. This type of fusion permits a rapid and efficient purification of the recombinant products. For that, the sequences of the invention were expressed in the E. coli GT1 strain in the form of fusion proteins with GST according to the technique described by Smith and Johnson [Gene 67 (1988) 31]. Briefly, the Grb2 and Grb3-3 genes were first modified by introducing a BamHI site on either side of the start and stop codons. For that, the open reading frames of these genes were amplified by PCR by means of the following oligonucleotides:

```
Oligonucleotide I (5')(SEQ ID NO. 4):
GAATTCGGATCCATGGAAGCCATCGCCAAATATGACTTC

Oligonucleotide II (3')(SEQ ID NO. 5):
GAATTCGGATCCTTAGACGTTCCGGTTCACGGGGGTGAC
```

The underlined part corresponds to the BamHI site created, followed or preceded by the start and stop codons.

The genes thus amplified were then cloned in the form of BamHI fragments into the vector pGEX 2T (Pharmacia) linearized by the same enzyme, in 3' and in frame in a cDNA encoding GST. The vectors thus obtained were then used to transform the E. coli TG1 strain. The cells thus transformed were precultured overnight at 37° C., diluted 1/10 in LB medium, supplemented with IPTG in order to induce the expression (2 hours, 25° C.) and then cultured for about 21 hours at 25° C. The cells were then lysed, and the fusion proteins produced affinity-purified on an agarose-GHS column. For that, the bacterial lysate is incubated in the presence of the gel (prepared and equilibrated with lysis buffer) for 15 minutes at 4° C. After 3 washes with Tris-HCl buffer pH 7.4, the proteins are eluted in the presence of a tris-HCl buffer pH 7.7 containing an excess of GST. The supernatent is harvested and centrifuged.

The same procedure was used to prepare a mutant of Grb2 in which the glycine 203 is replaced by an arginine (Grb2G203R) and a Grb3-3 mutant in which the glycine 162 is replaced by an arginine (Grb3-3G162R). The Grb2G203R mutant has been described as no longer having any activity in a test of reinitiation of DNA synthesis (Lowenstein et al., previously cited). The Grb3-3G162R mutant carries the same mutation in the same position, and should therefore also be inactive.

These mutants were prepared by mutagenesis by PCR on the Grb2 and Grb3-3 genes using, in 5', the oligonucleotide I described above, and in 3', the following oligonucleotide III in which the mutated codon is underlined:

Oligonucleotide III (3') (SEQ ID No. 6):

GACGTTCCGGTTCACGGGGGTGACAT-AATTGCGGGGAAACATGCGGGTC

The fragments thus amplified were then eluted, reamplified by PCR by means of the oligonucleotides I and II, and then cloned into the vector pGEX 2T. The mutants were then produced as described above.

The GST fusion proteins (GST-Grb2, GST-Grb3-3, GST-Grb3-3G162R and GST) were then biotinylated by conventional techniques known to persons skilled in the art (cf. general molecular biology techniques as well as Mayer et al., PNAS 88 (1991) 627), and used as probes to determine the binding to the immobilized phosphorylated EGF receptor (2.1.) and then to a peptide derived from hSOS1 (2.2.).

2.1. Binding to the phosphorylated EGF receptor

Procedure: The EGF receptor used was purified from A431 cells by immobilization on WGA-sepharose according to the technique described by Duchesne et al., (Science 259 (1993) 525). 2 $\mu$g of this receptor were first stimulated by 1 $\mu$M EGF, 10 min at 22° C., and then incubated, with or without cold ATP (10 $\mu$M) in the presence of 2.5 mM $MnCl_2$ in HNTG buffer (20 mM Hepes, 150 mM NaCl, 0.1% Triton, 10% glycerol, pH=7.5) at 4° C. for 2 min. The phosphorylation of the receptor is then stopped by adding a degradation buffer. The samples are then deposited on a 4–20% SDS-PAGE gel and then transferred onto polyvinylidene difluoride membranes (PVDF). The blots were then incubated in the presence of various biotinylated GST fusions (2 $\mu$g/ml) and then revealed by means of alkaline-phosphatase coupled streptavidin (Promega). The EGF receptors were also subjected to an immunoblotting in the presence of anti-phosphotyrosine antibodies (anti-PY) in order to verify that the receptors have indeed been phosphorylated.

Results: The results obtained are presented in FIG. 2a. They show, as expected, that the Grb2 protein interacts with the EGF receptor in phosphorylated form alone. They also show that the Grb3-3 protein does not bind the EGF receptor, regardless of its degree of phosphorylation.

2.2. Binding to a peptide derived from hSOS1

Procedure: the following two proline-rich peptides were synthesized:

hSOS1 Peptide: GTPEVPVPPPVPPRRRPESA: This peptide corresponds to residues 1143 to 1162 of the hSOS1 protein (Li et al., Nature 363 (1993) 83) responsible for the interaction between Grb2 and hSOS1 (SEQ ID No. 7).

3BP1 Peptide: PPPLPPLV: This peptide is derived from the 3BP1 protein, which is known to efficiently bind the SH3 domain of Ab1 and Src (Cicchetti et al., Science 257 (1992) 803)(SEQ ID No. 8).

Each of these peptides (1 $\mu$l, 10 mg/ml) was immobilized on nitrocellulose membrane. The membranes were then incubated in a blocking buffer (20 mM Tris pH=7.6, 150 mM NaCl, 0.1% Tween, 3% bovine albumin). The membranes were then incubated overnight at 4° C. in the presence of the various biotinylated GST fusions (4 $\mu$g/ml) and then revealed by means of alkaline phosphatase-coupled streptavidin (Promega).

Results: The results obtained are presented in FIG. 2b. They show that Grb3-3, like Grb2, is capable of binding the hSOS1 peptide. They also show that this interaction is specific since no binding is observed with the 3BP1 peptide. Moreover, the results also show that the Grb3-3G162R mutant is no longer capable of binding the hSOS1 peptide, which confirms the importance of this residue and the functional role of this interaction.

3. Activity of the Grb3-3 protein

This example demonstrates that, in spite of its deletion in the SH2 domain, the Grb3-3 protein has a functional effect.

The activity of the Grb3-3 protein was studied by determining its capacity to cooperate with ras for the transactivation of a promoter possessing ras response elements (RRE) and governing the expression of a reporter gene.

The procedure used has been described for example in Schweighoffer et al., Science 256 (1992) 825. Briefly, the promoter used is a synthetic promoter composed of the murine promoter of the thymidine kinase gene and 4 repeated PEA1 elements derived from the polyoma enhancer (Wasylyk et al., EMBO J. 7 (1988) 2475): Py-TK promoter. This promoter directs the expression of the reporter gene, in this case of the bacterial gene for chloramphenicol acetyl transferase (CAT): Py-TK-CAT vector. The vectors for expressing the tested genes were constructed by inserting the said genes, in the form of BamHI fragments, into the BglII site of the plasmid pSV2. This site makes it possible to place the genes under the control of the early SV40 promoter.

ER22 cells which are 40% confluent were transfected with 0.5 $\mu$g of the vector Py-TK-CAT alone (Py) or in the presence of the expression vector carrying, under the control of the early SV40 promoter, the gene: Grb2, 2 $\mu$g, Grb3-3, 2 $\mu$g, Grb2(G203R) 2 $\mu$g, Grb3-3(G162R) 2 $\mu$g, or Grb3-3, 2 $\mu$g+Grb2, 2 $\mu$g. In each case, the total quantity of DNA was adjusted to 5 $\mu$g with an expression vector without insert. The transfection was carried out in the presence of lipospermine (Transfectam, IBF-Sepracor). The cells were maintained for 48 hours in culture in a DMEM medium supplemented with 0.5% foetal calf serum. The CAT activity (transactivation of the RER) was then determined as described by Wasylyk et al. (PNAS 85 (1988) 7952).

The results obtained are presented in FIG. 3. They show clearly that the expression of the Grb3-3 protein prevents the effects of the activation of a growth factor receptor. They also show that Grb2 in excess prevents the effects of Grb3-3 on the response to the growth factor.

4. Grb3-3 induces cellular apoptosis

This example demonstrates the direct involvement of Grb3-3 in cellular apoptosis. This property offers particularly advantageous applications for the treatment of pathologies resulting from a cellular proliferation (cancers, restenosis, and the like).

The induction of cellular apoptosis by Grb3-3 was demonstrated (i) by injecting recombinant protein into 3T3 fibroblasts and (ii) by transferring the Grb3-3 encoding sequence into the 3T3 cells.

(i) Injection of the recombinant protein

The recombinant Grb3-3 protein was prepared in the form of fusion protein with GST according to the procedure described in Example 2. The fusion protein was then treated with thrombin (0.25%, Sigma) in order to separate the GST part, and then purified by ion-exchange chromatography on a monoQ column. The fractions containing the recombinant protein were then concentrated by means of Microsep microconcentrators (Filtron) in a 20 mM phosphate buffer (pH 7) containing 100 mM NaCl. The purified protein thus obtained was injected (1 to 3 mg/ml) into cultured 3T3 cells by means of an automatic Eppendorf microinjector. The cells were then incubated at 34° C. and photographed at regular intervals in order to follow the morphological transformations. The results obtained show that 5 hours after the injection of Grb3-3, most of the cells were dead whereas the injection under the same conditions of Grb2 or of the Grb3-3 mutant (G162R) had no effect on the viability of the cells.

(ii) Transfer of the sequence encoding the recombinant protein

A plasmid was constructed comprising the sequence SEQ ID No. 1 encoding the Grb3-3 protein under the control of the early promoter of the SV40 virus.

The 3T3 fibroblasts which are 40% confluent were transfected in the presence of lipospermine (Transfectam, IBF-Sepracor) with 0.5 or 2 μg of this expression plasmid. 48 hours after the transfection, 50% of the cells were in suspension in the medium, and the remaining cells, adhering to the wall, exhibited very substantial morphological changes (FIG. 4). Analysis by agarose gel electrophoresis showed, moreover, that the cells had an oligo-nucleosomal DNA fragmentation pattern characteristic of dead cells (FIG. 4). In contrast, the cells transfected under the same conditions with a Grb2, Grb3-3 (G162R) or Grb2 (G203R) expression plasmid retain a normal morphology, are always viable and show no DNA fragmentation. As shown in FIG. 4, the co-expression of Grb2 makes it possible to prevent the effects of Grb3-3.

These results therefore clearly show that Grb3-3 constitutes a killer gene capable of inducing cellular apoptosis. As indicated above, this property offers particularly advantageous applications for the treatment of pathologies resulting from a cellular proliferation such as especially cancers, restenosis and the like.

5. Demonstration of the expression of Grb3-3 in lymphocytes infected by the HIV virus This example shows that, during the cycle for infection of the T lymphocytes by the HIV virus, the relative proportion of the Grb2 and Grb3-3 mRNAs is modified, and that the Grb3-3 messenger is overexpressed at the time of massive viral production and cell death.

Peripheral blood lymphocytes were infected with the HIV-1 virus at two dilutions (1/10 and 1/100) for 1, 4 or 7 days. The mRNAs from the cells were then analysed by inverse-PCR by means of oligonucleotides specific for Grb2 and Grb3-3 in order to determine the relative proportion of the Grb2 and Grb3-3 messengers. The Grb3-3-specific oligonucleotides used are the following:

```
Oligonucleotide IV (3'):
ATCGTTTCCAAACGGATGTGGTTT (SEQ ID NO. 9)

Oligonucleotide V (5'):
ATAGAAATGAAACCACATCCGTTT (SEQ ID NO. 10)
```

The results obtained are presented in FIG. 5. They show clearly that 7 days after the infection with the HIV virus, the Grb3-3 MRNA is overexpressed. As shown by assaying the p24 protein and the virus reverse transcriptase, day 7 also corresponds to the period during which a massive viral production is observed.

SEQUENCE LISTING

```
(1) GENERAL INFORMATION:

   (iii) NUMBER OF SEQUENCES: 10


(2) INFORMATION FOR SEQ ID NO: 1:

     (i) SEQUENCE CHARACTERISTICS:
          (A) LENGTH: 933 base pairs
          (B) TYPE: nucleic acid
          (C) STRANDEDNESS: double
          (D) TOPOLOGY: linear

    (ii) MOLECULE TYPE: cDNA

    (ix) FEATURE:
          (A) NAME/KEY: CDS
          (B) LOCATION: 37..567

    (ix) FEATURE:
          (A) NAME/KEY: misc_feature
          (B) LOCATION: 37..567
          (D) OTHER INFORMATION: /product= "Grb3-3"

    (xi) SEQUENCE DESCRIPTION: SEQ ID NO: 1:

GAATTCGGGG CTGCTGAGCA CTGAGCAGGG CTCAGA ATG GAA GCC ATC GCC AAA       54
                                        Met Glu Ala Ile Ala Lys
                                          1               5

TAT GAC TTC AAA GCT ACT GCA GAC GAC GAC CTG AGC TTC AAA AGG GGG      102
Tyr Asp Phe Lys Ala Thr Ala Asp Asp Asp Leu Ser Phe Lys Arg Gly
            10                  15                  20

GAC ATC CTC AAG GTT TTG AAC GAA GAA TGT GAT CAG AAC TGG TAC AAG      150
Asp Ile Leu Lys Val Leu Asn Glu Glu Cys Asp Gln Asn Trp Tyr Lys
        25                  30                  35

GCA GAG CTT AAT GGA AAA GAC GGC TTC ATT CCC AAG AAC TAC ATA GAA      198
Ala Glu Leu Asn Gly Lys Asp Gly Phe Ile Pro Lys Asn Tyr Ile Glu
    40                  45                  50

ATG AAA CCA CAT CCG TTT GGA AAC GAT GTG CAG CAC TTC AAG GTG CTC      246
Met Lys Pro His Pro Phe Gly Asn Asp Val Gln His Phe Lys Val Leu
```

-continued

```
 55                  60                  65                  70

CGA GAT GGA GCC GGG AAG TAC TTC CTC TGG GTG GTG AAG TTC AAT TCT      294
Arg Asp Gly Ala Gly Lys Tyr Phe Leu Trp Val Val Lys Phe Asn Ser
                 75                  80                  85

TTG AAT GAG CTG GTG GAT TAT CAC AGA TCT ACA TCT GTC TCC AGA AAC      342
Leu Asn Glu Leu Val Asp Tyr His Arg Ser Thr Ser Val Ser Arg Asn
             90                  95                 100

CAG CAG ATA TTC CTG CGG GAC ATA GAA CAG GTG CCA CAG CAG CCG ACA      390
Gln Gln Ile Phe Leu Arg Asp Ile Glu Gln Val Pro Gln Gln Pro Thr
        105                 110                 115

TAC GTC CAG GCC CTC TTT GAC TTT GAT CCC CAG GAG GAT GGA GAG CTG      438
Tyr Val Gln Ala Leu Phe Asp Phe Asp Pro Gln Glu Asp Gly Glu Leu
    120                 125                 130

GGC TTC CGC CGG GGA GAT TTT ATC CAT GTC ATG GAT AAC TCA GAC CCC      486
Gly Phe Arg Arg Gly Asp Phe Ile His Val Met Asp Asn Ser Asp Pro
135                 140                 145                 150

AAC TGG TGG AAA GGA GCT TGC CAC GGG CAG ACC GGC ATG TTT CCC CGC      534
Asn Trp Trp Lys Gly Ala Cys His Gly Gln Thr Gly Met Phe Pro Arg
                155                 160                 165

AAT TAT GTC ACC CCC GTG AAC CGG AAC GTC TAA GAGTCAAGAA GCAATTATTT    587
Asn Tyr Val Thr Pro Val Asn Arg Asn Val  *
            170                 175

AAAGAAAGTG AAAAATGTAA AACACATACA AAAGAATTAA ACCCACAAGC TGCCTCTGAC    647

AGCAGCCTGT GAGGGAGTGC AGAACACCTG CCGGGTCACC CTGTGACCCT CTCACTTTGG    707

TTGGAACTTT AGGGGGTGGG AGGGGGCGTT GGATTTAAAA ATGCCAAAAC TTACCTATAA    767

ATTAAGAAGA GTTTTTATTA CAAATTTTCA CTGCTGCTCC TCTTTCCCCT CCTTTGTCTT    827

TTTTTTCTTC CTTTTTTCTC TTCTGTCCAT CAGTGCATGA CGTTTAAGGC CACGTATAGT    887

CCTAGCTGAC GCCAATAAAA AACAAGAAAC CAAAAAACCC GAATTC                   933
```

(2) INFORMATION FOR SEQ ID NO: 2:

(i) SEQUENCE CHARACTERISTICS:
(A) LENGTH: 176 amino acids
(B) TYPE: amino acid
(D) TOPOLOGY: linear (ii) MOLECULE TYPE: protein (xi) SEQUENCE DESCRIPTION: SEQ ID NO: 2:

```
Met Glu Ala Ile Ala Lys Tyr Asp Phe Lys Ala Thr Ala Asp Asp Asp
  1               5                  10                  15

Leu Ser Phe Lys Arg Gly Asp Ile Leu Lys Val Leu Asn Glu Glu Cys
             20                  25                  30

Asp Gln Asn Trp Tyr Lys Ala Glu Leu Asn Gly Lys Asp Gly Phe Ile
         35                  40                  45

Pro Lys Asn Tyr Ile Glu Met Lys Pro His Pro Phe Gly Asn Asp Val
     50                  55                  60

Gln His Phe Lys Val Leu Arg Asp Gly Ala Gly Lys Tyr Phe Leu Trp
 65                  70                  75                  80

Val Val Lys Phe Asn Ser Leu Asn Glu Leu Val Asp Tyr His Arg Ser
                 85                  90                  95

Thr Ser Val Ser Arg Asn Gln Gln Ile Phe Leu Arg Asp Ile Glu Gln
            100                 105                 110

Val Pro Gln Gln Pro Thr Tyr Val Gln Ala Leu Phe Asp Phe Asp Pro
        115                 120                 125

Gln Glu Asp Gly Glu Leu Gly Phe Arg Arg Gly Asp Phe Ile His Val
```

-continued

```
    130                 135                 140

Met Asp Asn Ser Asp Pro Asn Trp Trp Lys Gly Ala Cys His Gly Gln
145                 150                 155                 160

Thr Gly Met Phe Pro Arg Asn Tyr Val Thr Pro Val Asn Arg Asn Val
                165                 170                 175


(2) INFORMATION FOR SEQ ID NO: 3:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligonucleotide"

    (xi) SEQUENCE DESCRIPTION: SEQ ID NO: 3:

ATGGAAGCCA TCGCCAAATA TGAC                                          24


(2) INFORMATION FOR SEQ ID NO: 4:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligonucleotide I"

    (xi) SEQUENCE DESCRIPTION: SEQ ID NO: 4:

GAATTCGGAT CCATGGAAGC CATCGCCAAA TATGACTTC                          39


(2) INFORMATION FOR SEQ ID NO: 5:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligonucleotide II"

    (xi) SEQUENCE DESCRIPTION: SEQ ID NO: 5:

GAATTCGGAT CCTTAGACGT TCCGGTTCAC GGGGGTGAC                          39


(2) INFORMATION FOR SEQ ID NO: 6:

     (i) SEQUENCE CHARACTERISTICS:
          (A) LENGTH: 49 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligonucleotide III"

    (xi) SEQUENCE DESCRIPTION: SEQ ID NO: 6:

GACGTTCCGG TTCACGGGGG TGACATAATT GCGGGGAAAC ATGCGGGTC               49


(2) INFORMATION FOR SEQ ID NO: 7:

     (i) SEQUENCE CHARACTERISTICS:
          (A) LENGTH: 20 amino acids
          (B) TYPE: amino acid
          (C) STRANDEDNESS: <Unknown>
```

-continued

```
          (D) TOPOLOGY: linear

    (ii) MOLECULE TYPE: peptide

     (v) FRAGMENT TYPE: internal

    (ix) FEATURE:
          (A) NAME/KEY: Peptide
          (B) LOCATION: 1..20
          (D) OTHER INFORMATION: /note= "hSOS1 peptide (residues
               1143-1162)"

    (xi) SEQUENCE DESCRIPTION: SEQ ID NO: 7:

Gly Thr Pro Glu Val Pro Val Pro Pro Pro Val Pro Pro Arg Arg Ar
1               5                   10                  15

Pro Glu Ser Ala
            20


(2) INFORMATION FOR SEQ ID NO: 8:

     (i) SEQUENCE CHARACTERISTICS:
          (A) LENGTH: 8 amino acids
          (B) TYPE: amino acid
          (C) STRANDEDNESS: <Unknown>
          (D) TOPOLOGY: linear

    (ii) MOLECULE TYPE: peptide

     (v) FRAGMENT TYPE: internal

    (ix) FEATURE:
          (A) NAME/KEY: Peptide
          (B) LOCATION: 1..8
          (D) OTHER INFORMATION: /note= "3BP1 peptide"

    (xi) SEQUENCE DESCRIPTION: SEQ ID NO: 8:

Pro Pro Pro Leu Pro Pro Leu Val
1               5


(2) INFORMATION FOR SEQ ID NO: 9:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligonucleotide IV"

    (xi) SEQUENCE DESCRIPTION: SEQ ID NO: 9:

ATCGTTTCCA AACGGATGTG GTTT                                          24


(2) INFORMATION FOR SEQ ID NO: 10:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "oligonucleotide V"

    (xi) SEQUENCE DESCRIPTION: SEQ ID NO: 10:

ATAGAAATGA AACCACATCC GTTT                                          24
```

We claim:

1. An isolated polynucleotide selected from the group consisting of:

a) a polynucleotide which encodes a polypeptide comprising the uninterrupted sequence SEQ ID NO: 2, and b) the complementary strand of a polynucleotide as defined in a).

2. The polynucleotide of claim 1, comprising nucleotides 37–564 of SEQ ID NO: 1 or the complementary strand of nucleotides 37–564 of SEQ ID NO: 1.

3. The polynucleotide of claim 1 comprising the sequence SEQ ID NO: 1 or the complementary strand of SEQ ID NO:1.

4. An antisense polynucleotide comprising a polynucleotide of claim 1, part b, wherein said antisense polynucleotide inhibits the expression of Grb2 and Grb3-3.

5. An antisense polynucleotide comprising all or part of the polynucleotide of claim 1, part b, wherein said antisense polynucleotide specifically inhibits the expression of Grb3-3.

6. A vector comprising a polynucleotide according to claim 1.

7. A vector according to claim 6, wherein said vector is a viral vector.

8. A vector according to claim 7, selected from the group consisting of adenoviruses, retroviruses, adeno-associated viruses, herpes virus, cytomegalovirus and vaccinia virus.

9. A vector according to claim 8, wherein the virus is defective for replication.

10. A composition comprising a vector according to claim 6 in a pharmaceutically acceptable carrier.

11. A composition comprising a polynucleotide according to claim 1 complexed with DEAE-dextran, nuclear proteins or lipids, or incorporated into liposomes.

12. An isolated polypeptide having the sequence SEQ ID NO: 2.

13. A composition comprising a polypeptide according to claim 12 in a pharmaceutically acceptable carrier.

14. An antisense polynucleotide according to claim 5, [and comprising] *wherein the polynucleotide comprises the complementary strand of* the sequence joining the N-terminal SH3 domain and the residual SH2 domain of Grb3-3.

15. An antisense RNA comprising a sequence complementary to all or part of a polynucleotide of claim 1, part a, wherein said antisense RNA specifically inhibits the expression of Grb3-3.

[16. An antisense RNA according to claim 15, and comprising the sequence joining the N-terminal SH3 domain and the residual SH2 domain of Grb3-3.]

17. An antisense RNA comprising a polynucleotide of claim 1, part b, wherein said antisense RNA inhibits the expression of Grb2 and Grb3-3.

*18. A process for expressing Grb3-3 in a host cell, comprising introducing the vector according to claim 6 into the host cell.*

*19. A process for expressing Grb3-3 in a host cell, comprising introducing the vector according to claim 7 into the host cell.*

*20. A process for expressing Grb3-3 in a host cell, comprising introducing the vector according to claim 8 into the host cell.*

*21. A process for expressing Grb3-3 in a host cell, comprising introducing the vector according to claim 9 into the host cell.*

*22. The process according to claim 18, wherein the host cell is a prokaryotic cell.*

*23. The process according to claim 22, wherein the prokaryotic cell is E. coli.*

*24. The process according to claim 18, wherein the host cell is a eukaryotic cell.*

*25. A process for preparing a Grb3-3 polypeptide, comprising transforming a host cell with a vector according to claim 6, culturing the host cell under conditions permitting expression of the Grb3-3 polypeptide, and recovering the Grb3-3 polypeptide.*

*26. A process for preparing a Grb3-3 polypeptide, comprising transforming a host cell with a vector according to claim 7, culturing the host cell under conditions permitting expression of the Grb3-3 polypeptide, and recovering the Grb3-3 polypeptide.*

*27. A process for preparing a Grb3-3 polypeptide, comprising transforming a host cell with a vector according to claim 8, culturing the host cell under conditions permitting expression of the Grb3-3 polypeptide, and recovering the Grb3-3 polypeptide.*

*28. A process for preparing a Grb3-3 polypeptide, comprising transforming a host cell with a vector according to claim 9, culturing the host cell under conditions permitting expression of the Grb3-3 polypeptide, and recovering the Grb3-3 polypeptide.*

*29. The process according to claim 25, wherein the host cell is a prokaryotic cell.*

*30. The process according to claim 29, wherein the prokaryotic cell is E. coli.*

*31. An antisense RNA according to claim 15, wherein the polynucleotide comprises the complementary strand of the sequence joining the N-terminal SH3 domain and the residual SH2 domain of Grb3-3.*

* * * * *